(12) United States Patent
Coe

(10) Patent No.: US 11,540,722 B2
(45) Date of Patent: Jan. 3, 2023

(54) ETALON MID-INFRARED PROBE FOR SPECTROSCOPIC TISSUE DISCRIMINATION

(71) Applicant: OHIO STATE INNOVATION FOUNDATION, Columbus, OH (US)

(72) Inventor: James Coe, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 17/716,451

(22) Filed: Apr. 8, 2022

(65) Prior Publication Data
US 2022/0322947 A1 Oct. 13, 2022

Related U.S. Application Data

(60) Provisional application No. 63/173,005, filed on Apr. 9, 2021.

(51) Int. Cl.
*G01J 3/18* (2006.01)
*A61B 5/00* (2006.01)
*G01J 3/02* (2006.01)
*G02B 6/293* (2006.01)

(52) U.S. Cl.
CPC .......... *A61B 5/0075* (2013.01); *A61B 5/0084* (2013.01); *G01J 3/18* (2013.01); *G01J 3/02* (2013.01); *G02B 6/29359* (2013.01)

(58) Field of Classification Search
CPC .. G01J 3/00; G01J 3/18; A61B 5/0084; A61B 5/0075; G02B 6/29359; G01B 2290/25
See application file for complete search history.

(56) References Cited

U.S. PATENT DOCUMENTS

2005/0264808 A1* 12/2005 Wang .................... G01N 21/65
356/328
2006/0116562 A1 6/2006 Acosta et al.
(Continued)

FOREIGN PATENT DOCUMENTS

KR 101398835 5/2014
WO 2017161097 9/2017

OTHER PUBLICATIONS

Mount Wilson, "A Grating Spectrometer and Fabry-Perot Interferometer for Use in The 1 μm-5μm Wavelength Region", 1981 (Year: 1981).*

(Continued)

*Primary Examiner* — Maurice C Smith
(74) *Attorney, Agent, or Firm* — Meunier Carlin & Curfman LLC

(57) ABSTRACT

An etalon-based mid-infrared probe can be configured for spectroscopic tissue discrimination, such as between non-normal (e.g., cancerous) and normal (e.g., healthy) tissue. A broadband light source can be applied to the etalon to generate fringes at spectroscopic wavelengths of interest, which can be delivered to a tissue specimen via a fiber loop probe. A response signal can be spectral dispersed across a parallel array of detector pixels, such as using a diffraction grating, and signal processed for performing the tissue classification. A learning model can be trained, using full IR spectral data, for applying a reduced set of wavelengths for performing the spectroscopic tissue analysis and classification.

20 Claims, 13 Drawing Sheets

(56) References Cited

U.S. PATENT DOCUMENTS

2012/0033220 A1* 2/2012 Kotidis .......... G01N 21/35
356/445
2019/0110687 A1 4/2019 Coe et al.

OTHER PUBLICATIONS

A. Fercher, "Ophthalmic Laser Interferometry" Sep. 15, 1986, & Mount Wilson, (Year: 1986).*
International Search Report and Written Opinion issued for Application No. PCT/US2022/024039, dated Jun. 22, 2022.
Gasser, Christoph, et al. "Enhanced mid-infrared multi-bounce ATR spectroscopy for online detection of hydrogen peroxide using a supercontinuum laser." *Optics Express* 26.9 (2018): 12169-12179.

* cited by examiner

ETALON MID-INFRARED PROBE FOR SPECTROSCOPIC TISSUE DISCRIMINATION

CROSS-REFERENCE TO RELATED APPLICATIONS

This application claims benefit of U.S. Provisional Application No. 63/173,005, filed Apr. 9, 2021, which is hereby incorporated herein by reference in its entirety.

TECHNICAL FIELD

This document pertains generally, but not by way of limitation, to spectroscopic tissue analysis, and more particularly, but not by way of limitation to an etalon parallel sampler mid-infrared probe for spectroscopic tissue discrimination.

BACKGROUND

Coe et al. U.S. Patent Application Publication No. US 2019/0110687 A1 entitled SYSTEM AND METHOD FOR THE DISCRIMINATION OF TISSUES USING A FAST INFRARED CANCER PROBE, which is hereby incorporated herein by reference, and which published on Apr. 18, 2019, relates to using an infrared (IR) probe and discriminating software to rapidly discriminate normal non-cancerous tissue from abnormal cancerous tissue.

SUMMARY

The present inventor has recognized, among other things, that it may be desirable to provide a more economical approach to tissue illumination and response sampling and spectroscopy than an approach using one or more tunable mid-infrared quantum cascade lasers (QCL). The present disclosure describes, among other things, a potentially more economical approach that can perform electromagnetic energy illumination of a tissue sample or specimen using an etalon and response electromagnetic energy parallel sampling from the tissue sample or specimen using an electromagnetic energy detector array.

The present computer-assisted methods or techniques may be used together with Support Vector Machines or other machine learning or other techniques for selecting a reduced wavelength set for performing spectroscopic tissue or other discrimination, and metrics for analyzing response electromagnetic energy detected from the tissue specimen, for example, such as using one or more of the techniques described in the above-incorporated Coe et al. U.S. Patent Application Publication No. US 2019/0110687. Such above-incorporated description of Coe et al. U.S. Patent Application Publication No. US 2019/0110687 describes, among other things, using discriminating software to rapidly discriminate abnormal tissue from normal tissue, such as during surgery, during physical examination of in situ lesions, and in assessing biopsy and resected tissue specimens. For example, such tissue discrimination can include discriminating cancerous from noncancerous tissues. The discriminating software, e.g., which can include metrics, algorithms, calibrant spectra, and decision equations, can allow tissue to be identified or classified as abnormal or normal, such as using a reduced set or even a minimum of infrared (IR) wavelengths in order to permit rapid measurements to be performed and analyzed, such as on a timescale fast enough for clinical use.

This summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This disclosure describes, among other things, an economical approach to mid-infrared spectroscopic tissue discrimination, such as which can include performing electromagnetic energy illumination of a tissue sample or specimen using an etalon and response electromagnetic energy parallel sampling from the tissue sample or specimen using an electromagnetic energy detector array.

For example, an "etalon" or Fabry-Perot cavity can include an optical or other electromagnetic energy device in which two parallel glass or other plates, such as each with approximately 10 nanometer thick metal or other reflective coatings, are situated or positioned at a specified spacing from each other, such as with the reflective surfaces facing each other. The specified spacing can be fixed or adjustably specifiable or variable, if desired, such as by an end-user. The resulting wavenumbers of the etalon, in air, can be represented as:

$$\tilde{v}_m = FSR \cdot m = \frac{m}{2dn} = \frac{m}{2d} \quad (1)$$

In Equation 1, m is the index of the fringe, FSR is the free spectral range, n is the index of refraction in the medium, which is effectively n=1 in air, and d is the specifiable etalon spacer distance.

Figure 1:
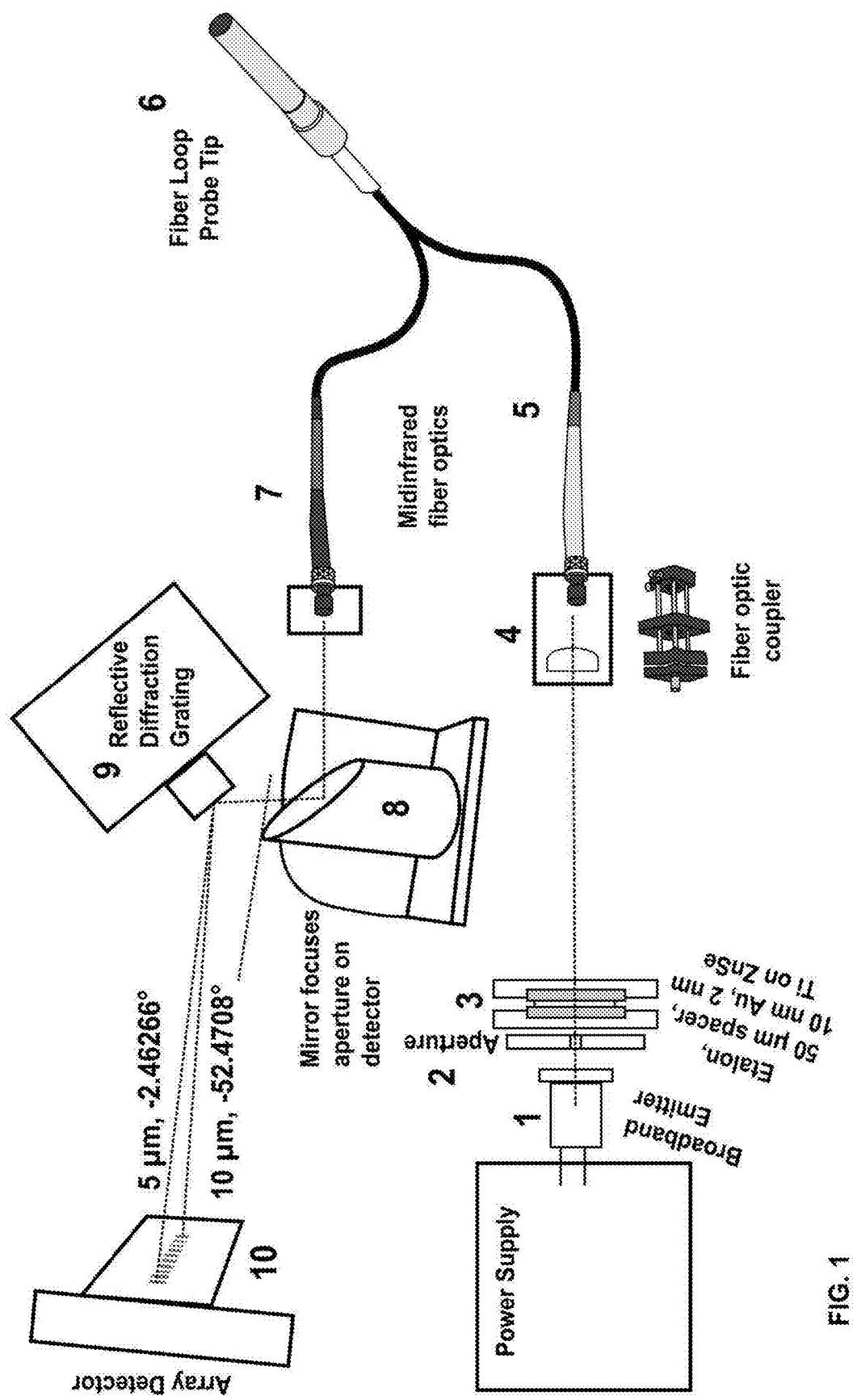
FIG. 1 is a schematic diagram illustrating generally an example of portions of a system employing an etalon that can be used for spectroscopy, such as for performing spectroscopic tissue discrimination.

FIG. 1 is a schematic diagram illustrating generally an example of portions of a system employing an etalon that can be used for spectroscopy, such as for performing spectroscopic tissue discrimination. In FIG. 1, a power supply can be configured to provide electrical power to a broadband emitter light source 1. A broadband electromagnetic energy output from the light source 1 can be directed through an aperture 2 in a baffle, barrier, or enclosure. The resulting spatially-constrained electromagnetic energy output from the aperture 2 can be directed onto an etalon 3. In the illustrative example of FIG. 1, the etalon 3 is shown with 50 µm spacing between reflectively coated parallel glass (or other material that is transparent at wavelengths of interest) plates. The desired spacing between plates can be established using a fixed or variable spacer, such as to obtain a desired specified thickness, between the plates. The reflective coating can include, for example, 10 nm thick gold (Au) that can be formed on a 2 nm thick titanium (Ti) layer that can be formed on facing Zinc Selenide (ZnSe) plates.

Figure 2:
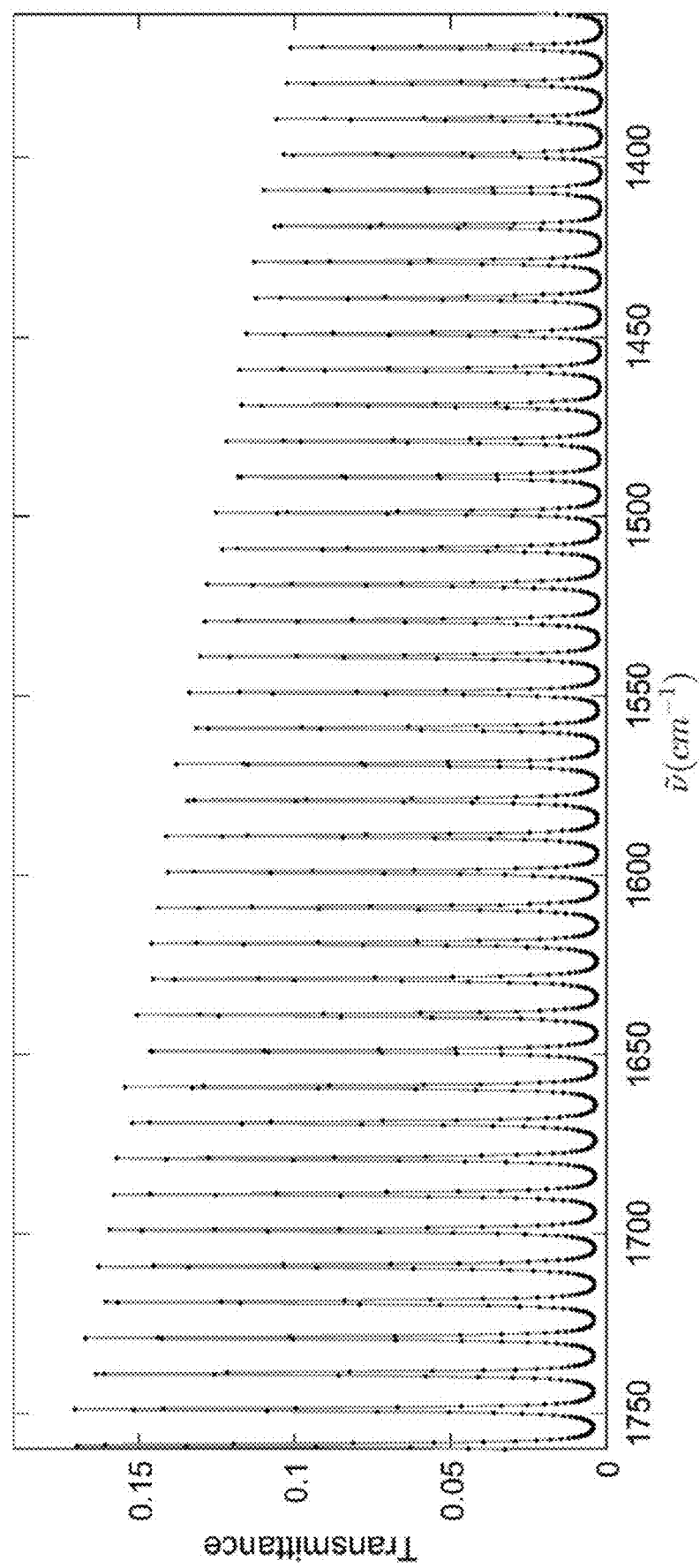
FIG. 2 is a graph of computer model predicted electromagnetic energy transmittance vs wavenumber ($cm^{-1}$) showing an illustrative example of equally-spaced (in in wavenumber) etalon illumination output fringes (high transmission peaks), such as can be produced by an etalon.

In response to the spatially constrained broadband electromagnetic energy received at its input, the etalon 3 can output equally-spaced (in wavenumber) emerging etalon electromagnetic energy peaks (e.g., referred to as "fringes"), such as shown in FIG. 2. The electromagnetic energy fringes emerging from the output of the etalon 3 can be received by and focused by refractive optics such as a fiber optic coupling lens 4, such as into a fiber optic bundle or cable 5. The fiber optic cable 5 can be configured to be capable of communicating mid-infrared electromagnetic energy to a fiber loop probe 6. A tip of the fiber loop probe 6 can be touched to a tissue specimen or other sample of interest. The fiber loop probe 6 tip can provide illumination to the tissue specimen or sample of interest, such as at the wavenumbers of the fringes output by the etalon 3. An absorbance or other tissue response characteristic of the tissue sample or specimen can be sensed by fiber loop probe 6 and the responsive electromagnetic energy signal can be communicated via an optical signal pathway toward a detector via a fiber optic bundle or cable 7. The fiber optic cable 7 can be configured to be capable of communicating mid-infrared electromagnetic energy along an optical signal pathway to receiving optics, such as a reflector or mirror 8. The mirror 8 can direct the electromagnetic energy response signal to a reflective diffraction grating 9 or other transmissive or reflector optical element capable of performing spatial separation of spectral wavelengths. The diffraction grating 9 can re-direct the spectrally-spread (e.g., diffracted) electromagnetic energy response signal onto an optical-to-electrical transducer such as a parallel array detector 10, such that the spectral content of the electromagnetic energy response signal is spread out across the different light detector pixels in the parallel array detector 10. The diffraction grating 9 can be configured to pass wavelengths from 5-10 µm across the array of pixels in the array detector, such as via a first order diffraction characteristic. The spacing between individual pixels in the array of pixels can be specified to correspond to the spacing resulting from the first order diffraction characteristic of the diffraction grating 9.

The individual detector pixels in the array of pixels in the array detector 10 can detect and transduce the spectrally dispersed response light to produce resulting respective electrical signals corresponding to the pixels. The resulting corresponding electrical signals output by the pixels of the array detector 10 can be communicated to signal processing circuitry for signal processing. For example, such signal processing circuitry can include analog front-end circuitry, followed by analog-to-digital conversion circuitry, which is, in turn, followed by digital signal processing circuitry. The digital signal processing can be implemented in a computer, which can be configured with a software algorithm to calculate one or more infrared metrics such as for performing spectroscopic analysis of the tissue specimen or sample being analyzed.

As shown in FIG. 1, the system employing the etalon 3 can permit the use of an inexpensive broadband emitter light source 1, rather than requiring a more expensive tunable QCL. The broadband emitter light source 1 can emit light with a variety of multiple wavelengths for input to the etalon 3. The etalon 3 can transform the light from the broadband emitter input light source 1, having the variety of multiple wavelengths, into a discrete number of equally-spaced wavenumber fringes that can be output by the etalon 3. An array detector 10 measures the response signal from a tissue sample of a specimen, such as from fiber loop probe 6 or other tissue interface device that illuminates and receives a response signal from contacting the tissue sample of the specimen. The response signal can be spectrally dispersed across the array detector 10, such as via the reflective diffraction grating 9, such that different spectral components are incident differently upon different individual ones of the pixels in the array detector 10.

For example, the individual ones of the pixels in the array detector 10 can be spaced apart from each other by specified spacing amounts that correspond to (1) the first order diffraction output angles at which diffracted light is emitted from the reflective diffraction grating 9 and the distance between the reflective diffraction grating 9 and the plane of the array detector 10, as described herein. The diffraction output angle at which diffracted light is emitted from the reflective diffraction grating 9 is represented in Equation (2) as:

$$\theta_m = \sin^{-1}(\sin \theta_i - m'\lambda/L), \quad (2)$$

where $\theta_i$ is the incident angle of light into the diffraction grating 9 (e.g., 45°), $\theta_m$ is the diffraction output angle from the diffraction grating 9, which depends on the grating spacing (L) between adjacent grating features, the wavelength of the incident light ($\lambda$), and the order of the diffraction grating (m') which can be specified to be 1 where first order diffraction outputs are desired.

An illustrative example of first order diffraction output angles for different wavenumbers (and corresponding wavelengths) for an etalon 3 having an output range of fringes at equally-spaced wavenumbers between 1000 cm-1 and 2000 cm-1, which is a useful range for tissue discrimination, is shown in Table 1 below.

TABLE 1

Diffraction output angle (degrees) vs. wavenumber (cm−1) and wavelength (micrometers) corresponding to etalon fringes.

| $\tilde{v}$ (cm$^{-1}$) | $\lambda$ (μm) | $\theta_m$ (°) |
|---|---|---|
| 1000 | 10 | −52.4708 |
| 1100 | 9.090909 | −41.0461 |
| 1200 | 8.333333 | −32.8893 |
| 1300 | 7.692308 | −26.5421 |
| 1400 | 7.142857 | −21.3724 |
| 1500 | 6.666667 | −17.0372 |
| 1600 | 6.25 | −13.3257 |
| 1700 | 5.882353 | −10.0981 |
| 1800 | 5.555556 | −7.25641 |
| 1900 | 5.263158 | −4.72917 |

Individual pixels in the detector array 10 can be arranged to receive first order diffraction of light emanating from the reflective diffraction grating at the corresponding diffraction output angles listed in Table 1. In this way, individual pixels in the detector array can detect response light corresponding to particular ones of the fringes of the etalon 3. As seen from Table 1, the spacings between individual pixels along the plane of the detector array 10 need not be equal for a detector array corresponding to an etalon having fringes that are equally-spaced in wavenumber. Instead, the spacing between individual pixels of the detector array 10 will be closer at shorter wavelengths (corresponding to larger wavenumbers) than at longer wavelengths (corresponding to smaller wavenumbers).

Figure 11:
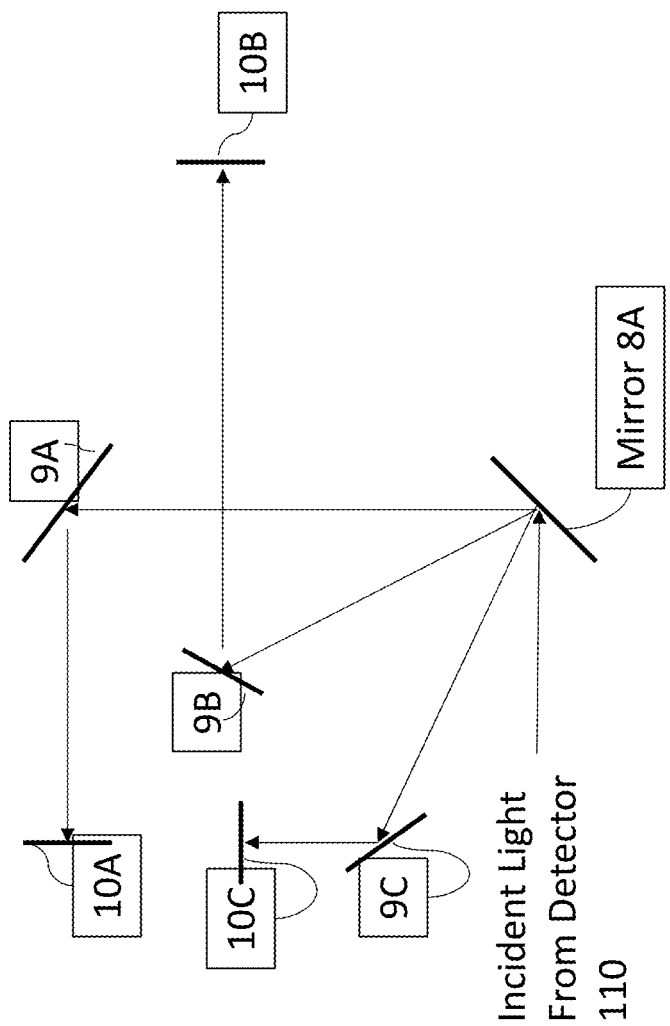
FIG. 11 illustrates an illustrative example such as which can include multiple mirrors, multiple diffraction gratings, multiple detector arrays, or any combination of these, which can be arranged in numerous ways, such as can include free space or fiber optic portions in one or more such arrangements.

Although FIG. 1 illustrates an example showing a single reflective diffraction grating 9 and a single detector array 10, either or both of these can include multiple devices, an illustrative non-limiting example of which is shown in FIG. 11. For example, multiple detector arrays 10 can be used with a single reflective grating 9, so that individual ones of the multiple detector arrays can be appropriately located to receive the desired first order (or higher order) diffracted output angles corresponding to fringes of the same etalon 3 or different instances of etalons 3 in a plurality of such etalons. Also by way of example, multiple reflective gratings 9 can be provided, such as to receive incident light from the same mirror 8 (at different angles of incidence as described in Equation 2) or from different mirrors 8 in an arrangement of multiple mirrors 8. A digital micromirror device (DMD) can be used to provide one or more of the mirrors 8. Individual ones of the gratings 9 (which need not be reflective, but which can also include a transmissive grating) can output diffracted light to one or more array detectors 10 corresponding to that particular grating 9 of the one or more gratings 9.

FIG. 2 is a graph of results of a computer TM simulation predicted electromagnetic energy transmittance vs wavenumber (cm$^{-1}$) showing an illustrative example of equally-spaced (in wavenumber) etalon illumination output fringes (high transmission peaks), such as can be produced by the etalon 3. The TM simulation results shown in the graph of FIG. 2 use the complex index of refraction of Au and Ti. FIG. 2 shows a 10 cm$^{-1}$ fringe spacing and a full-width-at-half-max of ~1.2 cm$^{-1}$ in the amide I mid-infrared region, using an etalon spacer of d=0.500 millimeters. Such fringes can be generated by the etalon 3 via multiple reflection interference of incident light into the etalon 3 from a broadband emitter light source 1. FIG. 2 shows an example in which the etalon illumination output fringes can provide a selective spectral output, such as equally spaced in wavenumber with a spectral resolution that is determined by the fringe width of the etalon 3. As shown in FIG. 2, the spectral resolution of the etalon illumination output can be better than a resolution available from an ordinary commercial infrared spectrometer. The resulting etalon illumination output wavelengths illustrated by the fringes in FIG. 2 can be output by the etalon 3 for delivery in parallel, such as for illuminating the tissue sample or specimen concurrently with multiple well-defined spectral illumination wavelengths corresponding to the fringes. Similarly, the response from the tissue sample or specimen to the different concurrent spectral illumination wavelengths of the corresponding fringes can also be detected concurrently in parallel, using an electromagnetic energy detector array 10. These techniques can help enable rapid spectroscopic analysis of tissue specimens, such as for helping provide rapid (e.g., real-time) results to a clinician, diagnostician, or other user in a clinical office setting, a pathology lab setting, or other appropriate setting.

Figure 3:
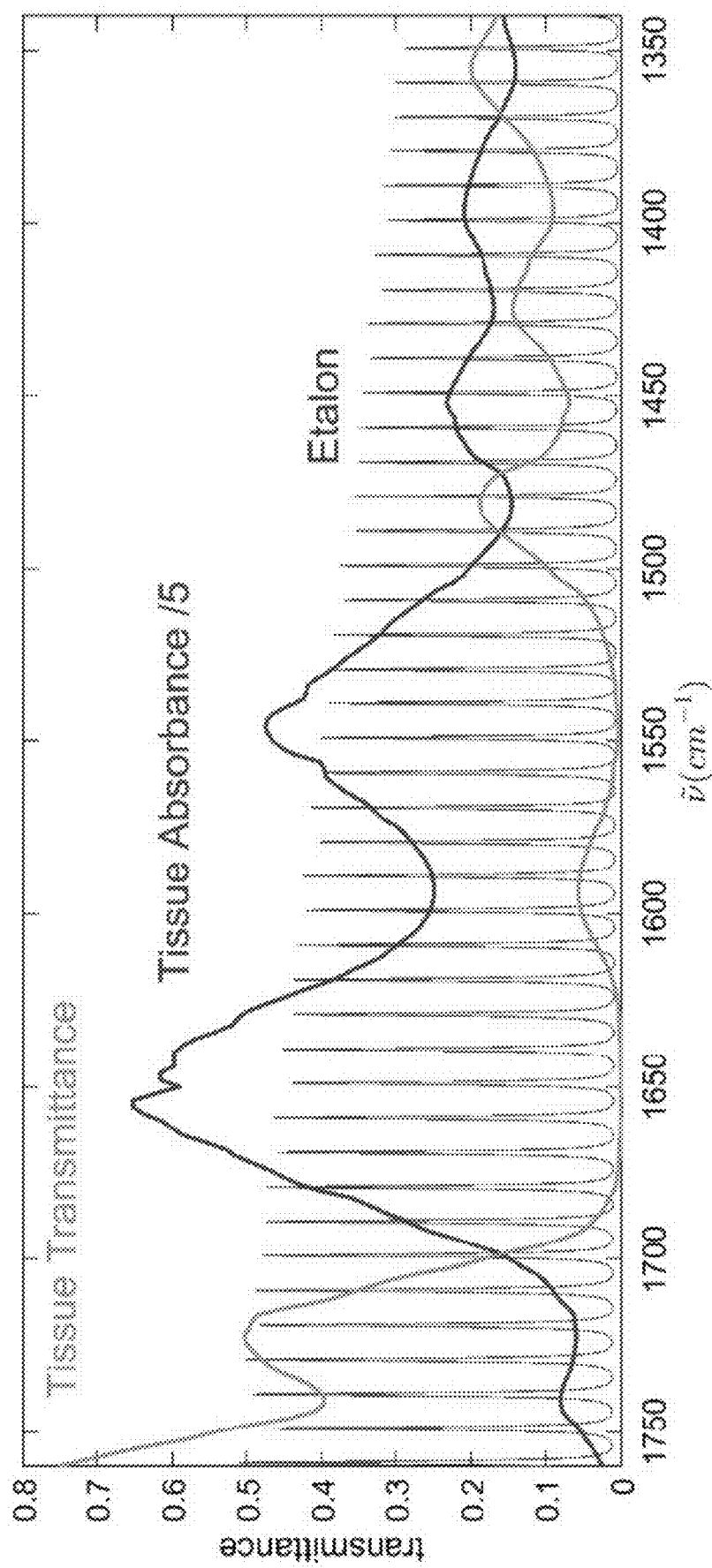
FIG. 3 shows an example of the TM simulated transmittance spectral graph of etalon fringes (red trace), similar to that shown in FIG. 2, but overlaid with the spectral graph of tissue absorbance (blue trace, scaled) and tissue transmittance (green trace).

FIG. 3 shows an example of the TM simulated transmittance spectral graph of etalon fringes (red trace), similar to that shown in FIG. 2, but overlaid with the spectral graph of tissue absorbance (blue trace, scaled by dividing by a scaling constant, e.g., divide by 5) and tissue transmittance (green trace). In FIG. 3, the intersections of the tissue absorbance and tissue transmittance characteristics depict how each will be sampled by the corresponding fringes provided by the etalon 3 to sample the tissue specimen or sample, such as using the probe 6 and the array detector 10.

Figure 4:
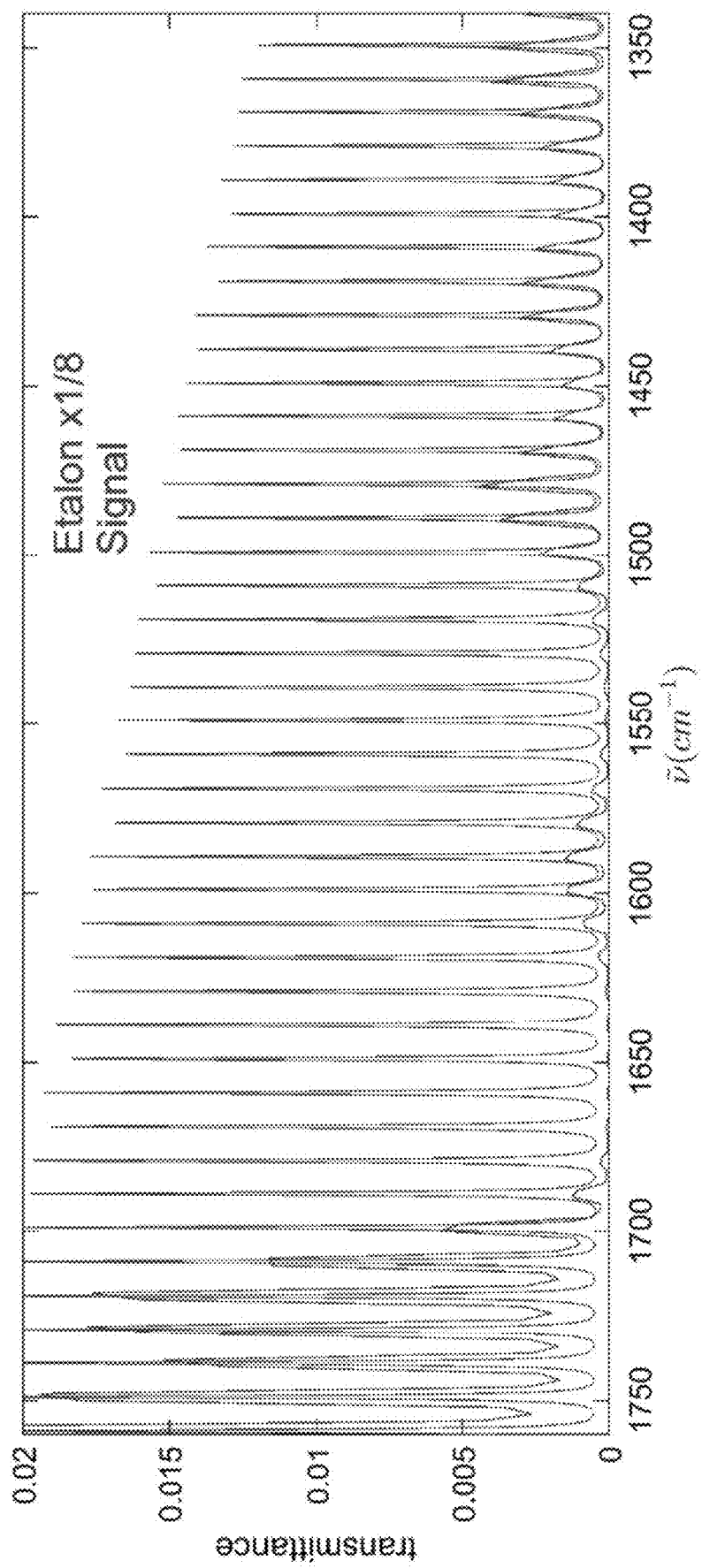
FIG. 4 shows a simulation of electromagnetic energy signal output from the etalon as fringes measured in air (red trace), and then again when the tip of the fiber loop probe is touched to the tissue sample of specimen (blue trace)

FIG. 4 shows a computer simulation of electromagnetic energy signal output transmission from the etalon 3 as (1) fringes measured in air (red trace, e.g., before the fiber loop probe 6 is touched to a tissue sample or specimen), and (2) then again when the tip of the fiber loop probe 6 is touched to the tissue sample of specimen (blue trace). The differential measurements between (1) and (2) at like wavenumber fringes can be used to determine an absorbance spectral characteristic of the tissue specimen at the corresponding wavenumbers of the fringes issued by the etalon 3.

Figure 5:
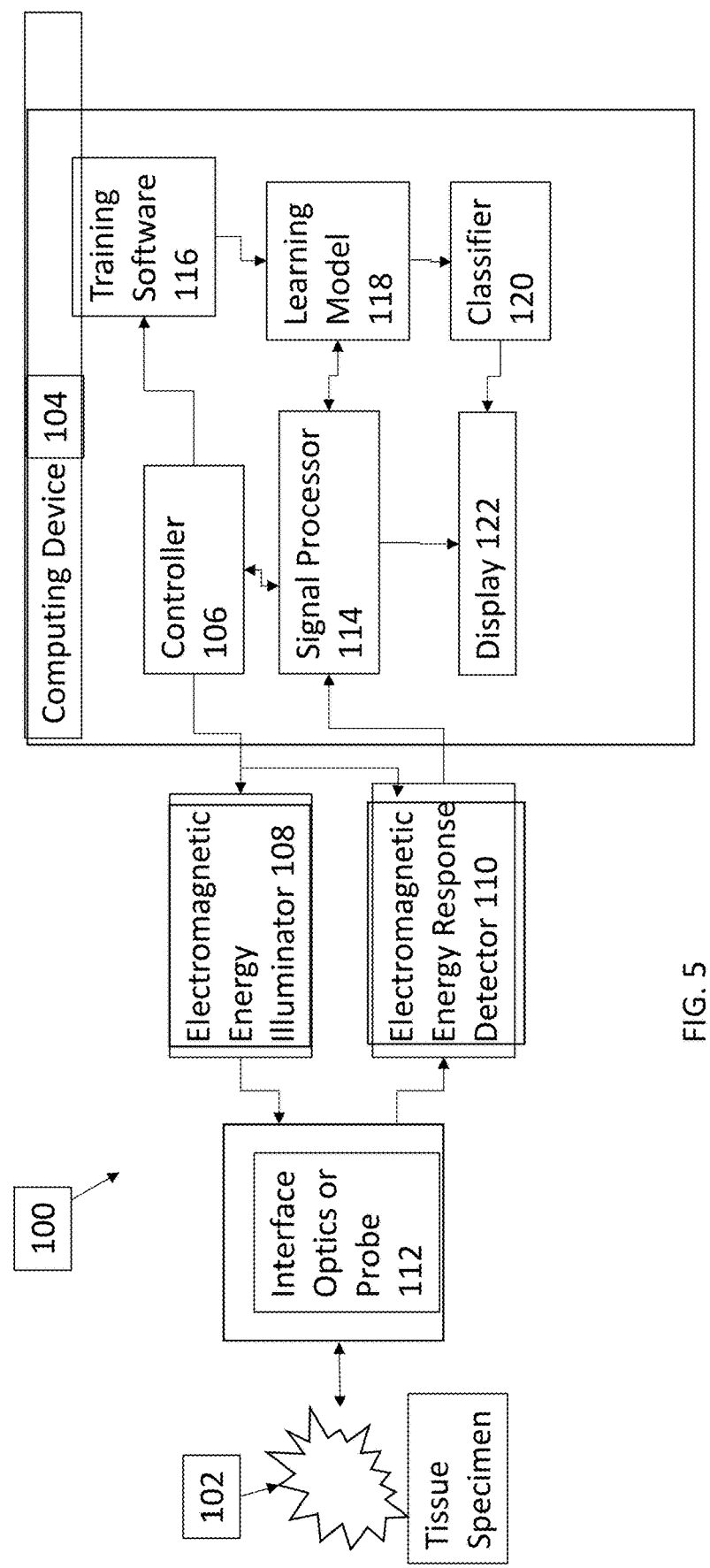
FIG. 5 is another view of portions of the system shown in FIG. 1, which can be represented as the system 100 shown in FIG. 5.

FIG. 5 is another view of portions of the system shown in FIG. 1, which can also be represented as the system 100 shown in FIG. 5. In system 100 of FIG. 5, the electromagnetic energy illuminator 108 can include the etalon 3, the electromagnetic energy response detector 110 can include the parallel sampling array detector 10, and the interface optics or probe 112 can include the fiber loop probe 6, an attenuated total reflection (ATR) crystal other suitable interface to the tissue specimen or other sample of interest for spectroscopic analysis and discrimination. Using an arrangement such as shown in FIG. 5, the measured absorbance metrics of the tissue specimen at the different wavenumbers can be used in a training mode, by training software 115, to train a learning model 118, such as using Support Vector Machines (SVM) decision equations, such as to discriminate between at least two classification categories such as cancerous and non-cancerous tissue using a classifier 120, such as in a manner similar to that described in Coe et al. U.S. Patent Application Publication No. US 2019/0110687 A1 entitled SYSTEM AND METHOD FOR THE DISCRIMINATION OF TISSUES USING A FAST INFRARED CANCER PROBE.

These measured absorbance metrics can be used to train SVM decision equations of the learning model 118 for tissue discrimination, such as between cancer and non-cancer. After training the learning model 118, the resulting decision equations can be used at run-time to evaluate new tissue specimens or samples 102 in subsequent tests using the system. This approach of the system shown in FIG. 1 and FIG. 5 can advantageously reduce the number of wavelengths that need be measured and, using the etalon 3 and the parallel sampling array detector 10, can measure these selected wavelengths in parallel for better measurement speed. Such parallel sampling measurements can retain the spectral resolution of the etalon 3, sampling at the wavenumbers of the fringes, and selectively reducing or avoiding spectral content of the response from the tissue sample or specimen at frequencies between wavenumbers corresponding to the fringes of the etalon 3.

Etalon Filtering Gaseous Water Effect for Emphasizing Protein Effect

As described in Equation 1, above, the spacing distance d can determine the spectral spacing between adjacent etalon fringe wavenumbers. The spacing distance d can be specifiable. The specifiable spacing distance d can be fixed or adjustable or selectable (e.g., such as by selecting between different etalons 3 such as can be included in the system 100). Although FIG. 2 shows fringes corresponding to an etalon spacing of d=10 $cm^{-1}$, other examples of etalons 3 can use a spacing distance d in a range between 10 $cm^{-1}$ and 60 $cm^{-1}$.

In addition to determining spectral spacing between etalon fringe wavenumbers using the spacing distance d, the parallel sampling array detector 110 can optionally selectively sample responses from the tissue sample corresponding to non-adjacent fringes, if desired, such as to skip response information from certain fringe wavenumbers. This can be done programmatically, such as ignoring electrical signal outputs from certain individual pixels of the array detector 10, or by locating or positioning individual pixels of the array detector 10 to only receive certain first order diffractions of response light corresponding to only certain fringes of light emitted by the etalon 3.

Regardless of whether done by selecting d on the illumination side of the system or by selecting a "digital offset" between the wavenumbers to be sampled by the parallel array detector 110 on the receive side of the system or by arranging individual pixels of the array detector 10 to only correspond to a subset of the fringes of light emitted by the etalon, or any of these, skipping wavenumbers can be utilized to filter unwanted "noise" data in the response from the tissue specimen or sample 102, such as that due to gaseous water. In an example of spectral response data from an SKH1 mouse skin cancer frozen section tissue slice, with tissue absorption data recorded at a resolution of 4 $cm^{-1}$ with 2 $cm^{-1}$ steps, as a digital offset between wavenumbers used is increased, an effect of gaseous water becomes less prominent, and a response associated with the protein features of the tissue is more in evidence. For example, the above-proposed use of a 10 $cm^{-1}$ spacing between measured wavenumbers of the etalon 3 will allow a very effective filtering of the gas phase water interference.

Reduced Range and SVM Analysis

Techniques similar to those described in the above-incorporated Coe et al. U.S. Patent Application Publication No. US 2019/0110687 A1 entitled SYSTEM AND METHOD FOR THE DISCRIMINATION OF TISSUES USING A FAST INFRARED CANCER PROBE can be used to train the learning model 118 to perform spectroscopic tissue discrimination using a reduced set of wavelengths from those investigated using full spectral data from an ATR probe, such as shown and described below with respect to FIG. 7. The above-incorporated Coe et al. U.S. Patent Application Publication No. US 2019/0110687 A1 entitled SYSTEM AND METHOD FOR THE DISCRIMINATION OF TISSUES USING A FAST INFRARED CANCER PROBE explained how to down-select from full IR spectral data to a reduced set of wavelengths that can fall within the output range of a single tunable QCL, such as using a trained learning model. After training, the single QCL can be operated at run-time to evaluate new tissue specimens or samples using the trained model with the down-selected set of wavelengths. Similarly techniques can be used during training a learning model to down-select to a suitable output range of an etalon 3. After training, the etalon 3 can be operated at the down-selected set of wavelengths, such as together with a parallel array sampler of the array detector 10, to evaluate new tissue specimens or samples.

Figure 6A:
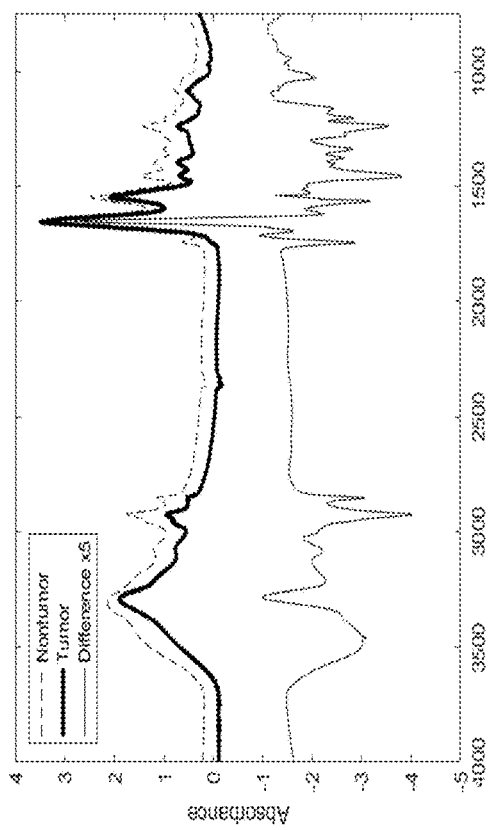
FIGS. 6A, 6B, and 6C illustrate an example in which full spectral SKH1 Mouse frozen tissue section data (FIG. 6A) was used to develop a SVM Beta spectrum (FIG. 6B), which was used to create a decision equation histogram (FIG. 6C).
Figure 6B:
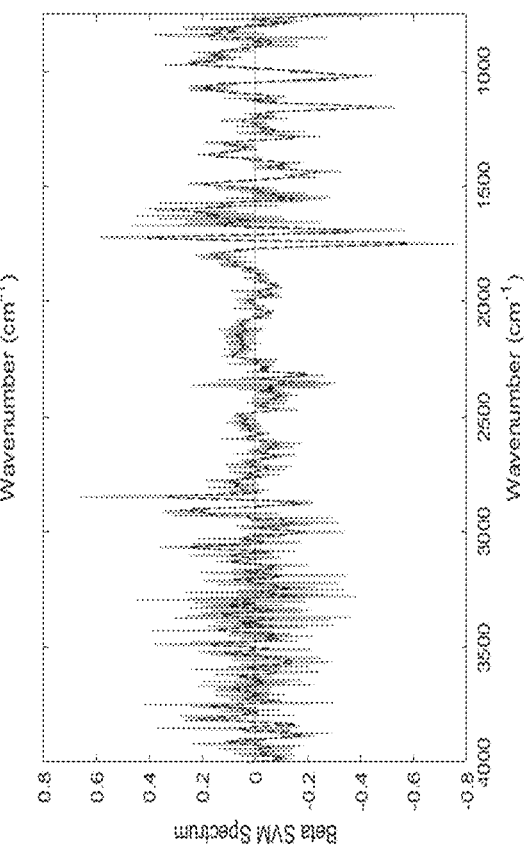
Figure 6C:
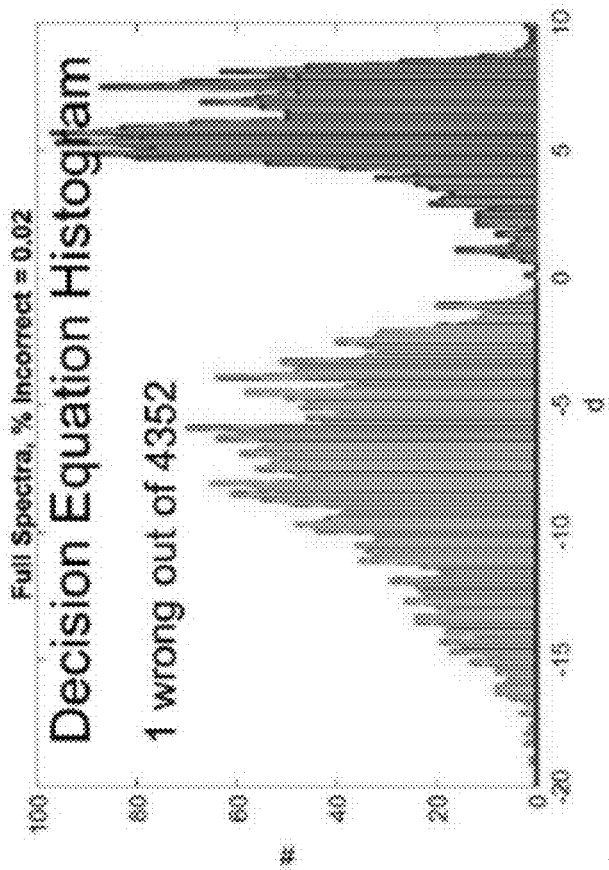

FIGS. 6A, 6B, and 6C illustrate an example in which fuller spectral SKH1 Mouse frozen tissue section data (FIG. 6A) was used to develop a SVM Beta spectrum (FIG. 6B), which was used to create a decision equation histogram (FIG. 6C) to assess the viability of a 160 $cm^{-1}$ reduced range of wavenumbers, such as of an etalon 3 with an equal spacing of 10 $cm^{-1}$ between adjacent wavenumbers corresponding with fringes emerging from the etalon 3. SVM analysis was done on the fuller spectral data set as shown in FIGS. 6A and 6B to form the decision equation histogram of FIG. 6C. The full spectral dataset included 4352 IR spectra to develop cancer vs. non-cancer decision equations using the 160 $cm^{-1}$ reduced range and 10 $cm^{-1}$ spacing between adjacent wavenumbers, with the reduced wavelength region resulting in only one tissue sample of 4352 tissue samples being classified incorrectly, as shown in the decision equation histogram of FIG. 6C. There are many evident differences in the IR spectrum of the tumor and nontumor regions, as shown in the absorbance vs. wavenumber data graphed in FIG. 6A, notably in the region from 1000 $cm^{-1}$ to 1500 $cm^{-1}$. FIG. 6B shows the SVM beta spectrum, which is positive at wavenumbers that are good at picking out tumor and negative for wavenumbers that are good at picking out non-tumor. In FIG. 6B, the curve overlaid with the Beta Spectrum shows broad and less noisy spectroscopic tissue discrimination features in the wavelength region from 1000-1500 $cm^{-1}$. Therefore, in an example, the etalon 3 can be operated to illuminate within in the wavelength region from 1000-1500 $cm^{-1}$, such as with wavelengths further down-selected to a 160 $cm^{-1}$ reduced range of wavenumbers of an etalon 3 with a spacing of 10 $cm^{-1}$ between adjacent wavenumbers corresponding with fringes emerging from the etalon 3.

ATR Probe Example

Figure 7:
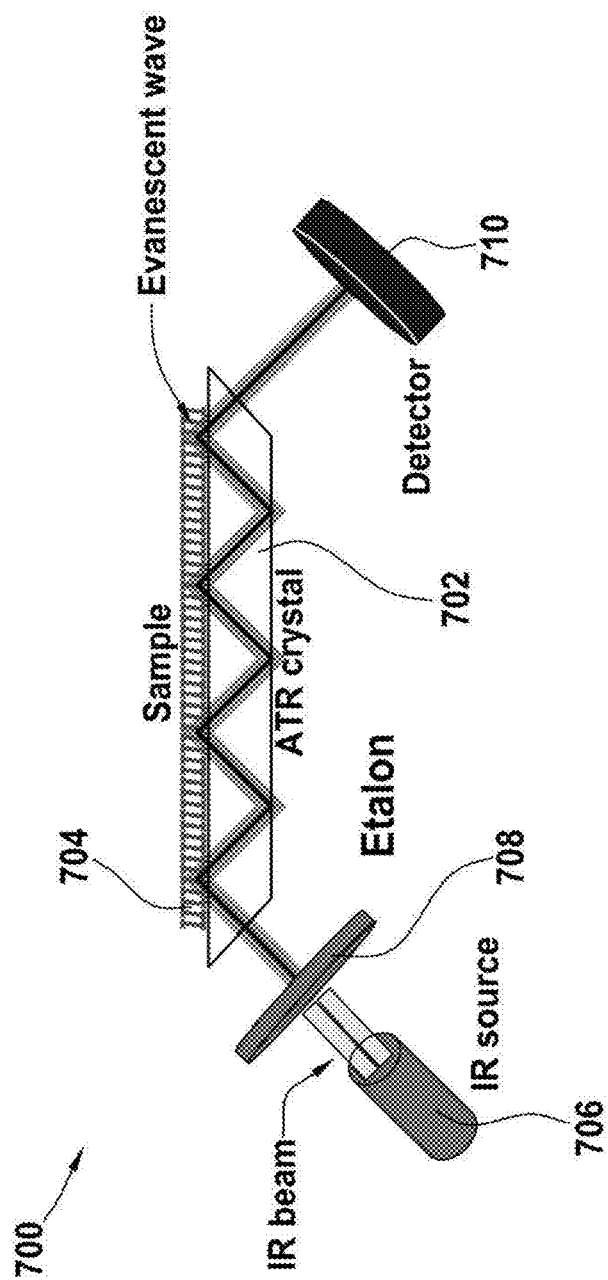
FIG. 7 shows an example of some possible variations of portions of the system such as shown and described with respect to FIGS. 1 and 5, such as with an Attenuated Total Reflection (ATR) crystal and with a suitable free-space arrangement of certain components instead of fiber optics.

FIG. 7 shows an example of some possible variations of portions of the system such as shown and described with respect to FIGS. 1 and 5, such as can include an arrangement 700 using an Attenuated Total Reflection (ATR) crystal 702 in the interface optics or probe 112 instead of the Fiber Loop Probe 6 shown in FIG. 1, and such as which can also include omitting certain fiber optics, if desired, with a suitable free-space arrangement of certain components. A fingertip or other tissue sample 704 can be placed upon the ATR crystal 702, such as for spectroscopic tissue analysis and discrimination. An electromagnetic energy source 706 can include a broadband emitter 1 and an aperture 2, which can provide light to an etalon 3, 708, such as similarly described with respect to and shown in FIG. 1. The etalon 3, 708 can output a resulting mid-IR beam of equally-spaced (in wavenumber) output fringes, such as similarly described above with respect to FIG. 1. The resulting IR beam can output the electromagnetic energy of the fringes for incoupling into the ATR crystal 702. Within the ATR crystal 702, the incoupled IR beam of electromagnetic energy at the fringe wavenumbers can form an evanescent wave that is impacted by absorption of the fingertip or other tissue sample 704 placed upon the ATR crystal 702, with such absorption characteristic useful for spectroscopic tissue analysis and discrimination of the sample 704. A detector 710 can detect IR electromagnetic energy emerging from the ATR crystal 702. The detector 710 can direct such response light through an arrangement of receiving optics, such as an arrangement that can be similar to the mirror 8, reflective diffraction grating 9, and array detector 10 of individual pixels, such as described with respect to and shown in FIG. 1.

Figure 8:
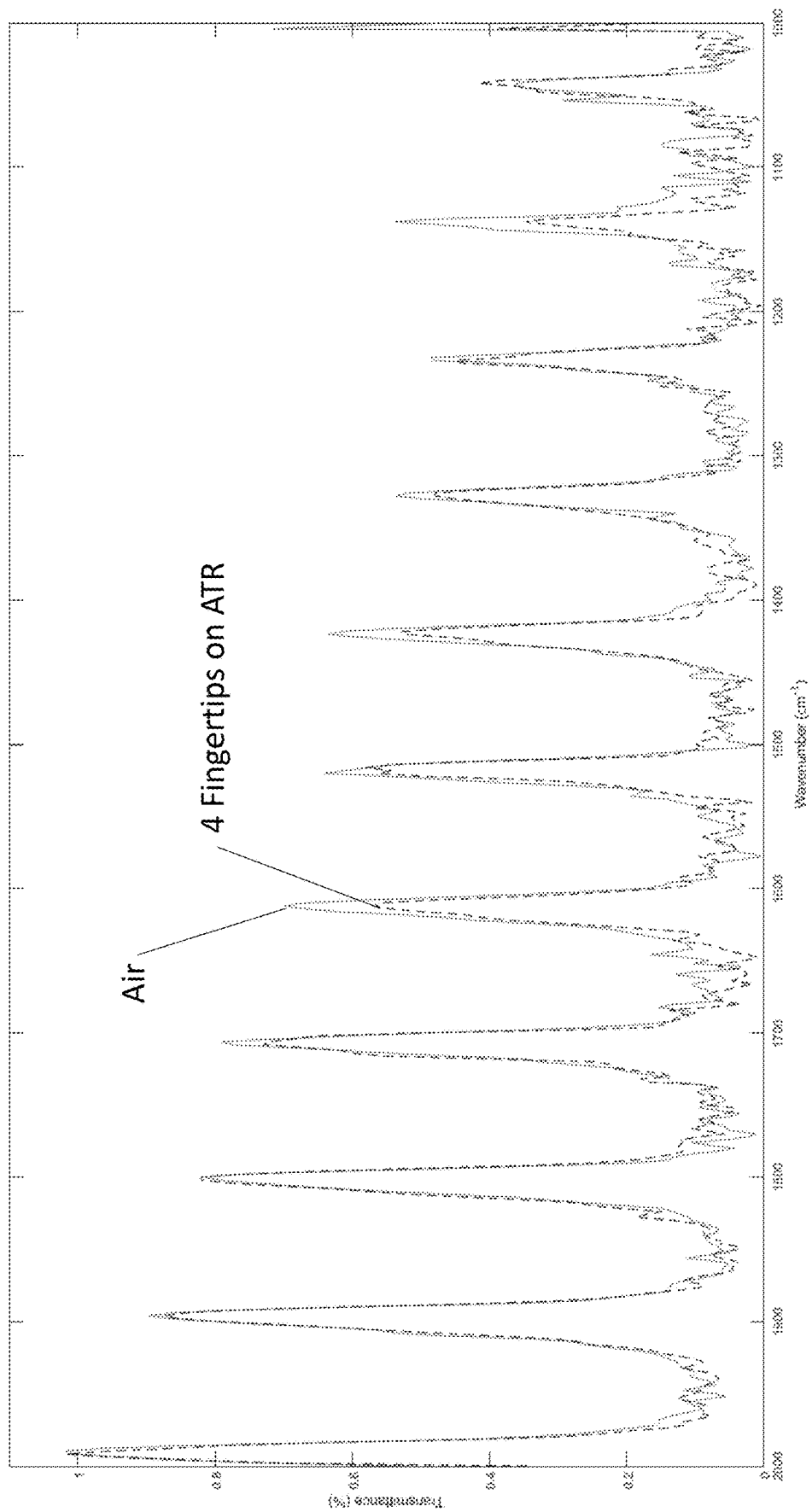
FIG. 8 is a graph of experimental data of Transmittance (%) vs. wavenumber ($cm^{-1}$) of response light from an arrangement using an ATR crystal such as that shown in FIG. 7

FIG. 8 is a graph of experimental data of Transmittance (%) vs. wavenumber ($cm^{-1}$) of response light from an arrangement using an ATR crystal 702 such as that shown in FIG. 7. In FIG. 8, detected electromagnetic energy responses are shown for (1) experimental data in which the ATR crystal 702 is merely exposed to air (denoted "AIR" in FIG. 8), without any tissue or other sample 704 being placed thereupon, and for (2) other experimental data in which the ATR crystal has four fingertips of a human subject placed onto the ATR crystal 702 (denoted "4 Finger Tips on ATR"). The difference between instances exposed to air (or a central tendency thereof) and instances exposed to fingertips is representative of an absorbance characteristic of the tissue of the fingertips placed onto the ATR crystal 702, such as shown in FIG. 9A.

Figure 9B:
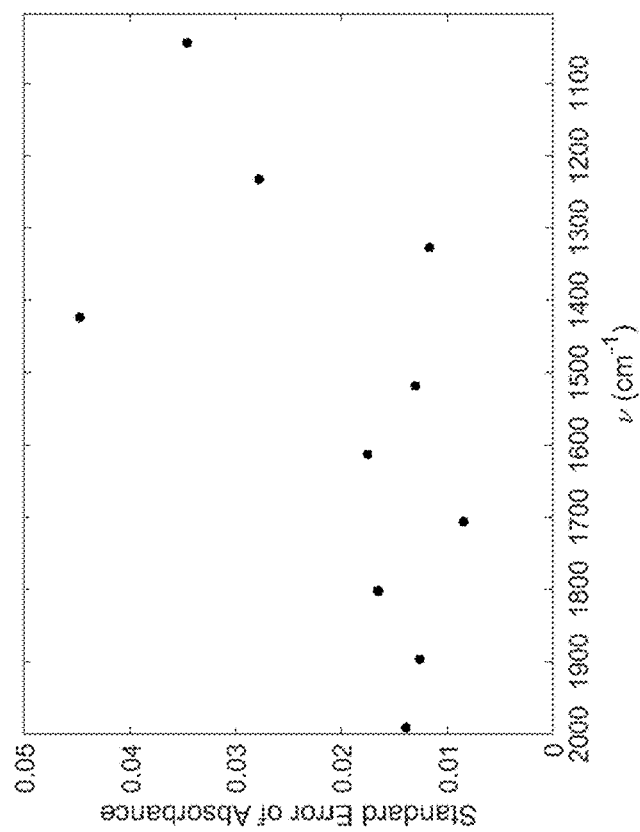
FIG. 9B is a graph of standard error of Absorbance vs. wavenumber for the corresponding experimental data shown in FIG. 9A.
Figure 9A:
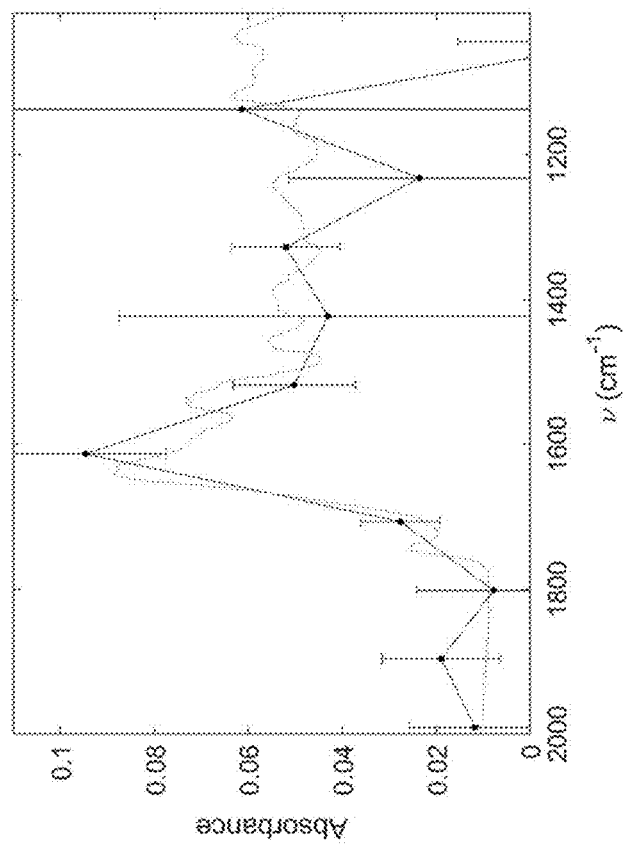
FIG. 9A is a graph of absorbance vs. wavenumber ($cm^{-1}$) corresponding to the experimental data shown in FIG. 8.

FIG. 9A is a graph of absorbance vs. wavenumber ($cm^{-1}$) corresponding to the experimental data shown in FIG. 8. In FIG. 9A, the four air measurements were used to estimate the error for the absorbance data measurements, which estimates are shown by the error bars in FIG. 9A. Absorbance (A) was calculated as shown in Equation 3:

$$A = -\log\left(\frac{I_{finger}}{I_{air}}\right), \quad (3)$$

where I is the response light intensity from the ATR crystal 702 with the fingers placed on the ATR crystal 702 ($I_{finger}$) and without the fingers placed on the ATR crystal 702 ($I_{air}$). The error in absorbance is as shown in Equation 4:

$$\Delta A = \frac{\Delta I}{2.3026}\sqrt{\frac{1}{I_{finger}^2} + \frac{1}{I_{air}^2}}, \quad (4)$$

where in Equation 4, $\Delta I$ is the corresponding error in measurements of either $I_{finger}$ or $I_{air}$.

FIG. 9B is a graph of standard error of Absorbance vs. wavenumber for the corresponding experimental data shown in FIG. 9A. As similarly explained with respect to FIG. 1, the response light from the different fringes can be spectrally dispersed, such as using a transmissive or reflective diffraction grating 9, and these spectrally dispersed fringe responses can be detected concurrently in parallel using appropriately placed individual pixel detectors of an array detector 10, thereby providing an etalon parallel sampler for performing spectroscopic tissue analysis and discrimination.

Figure 10A:
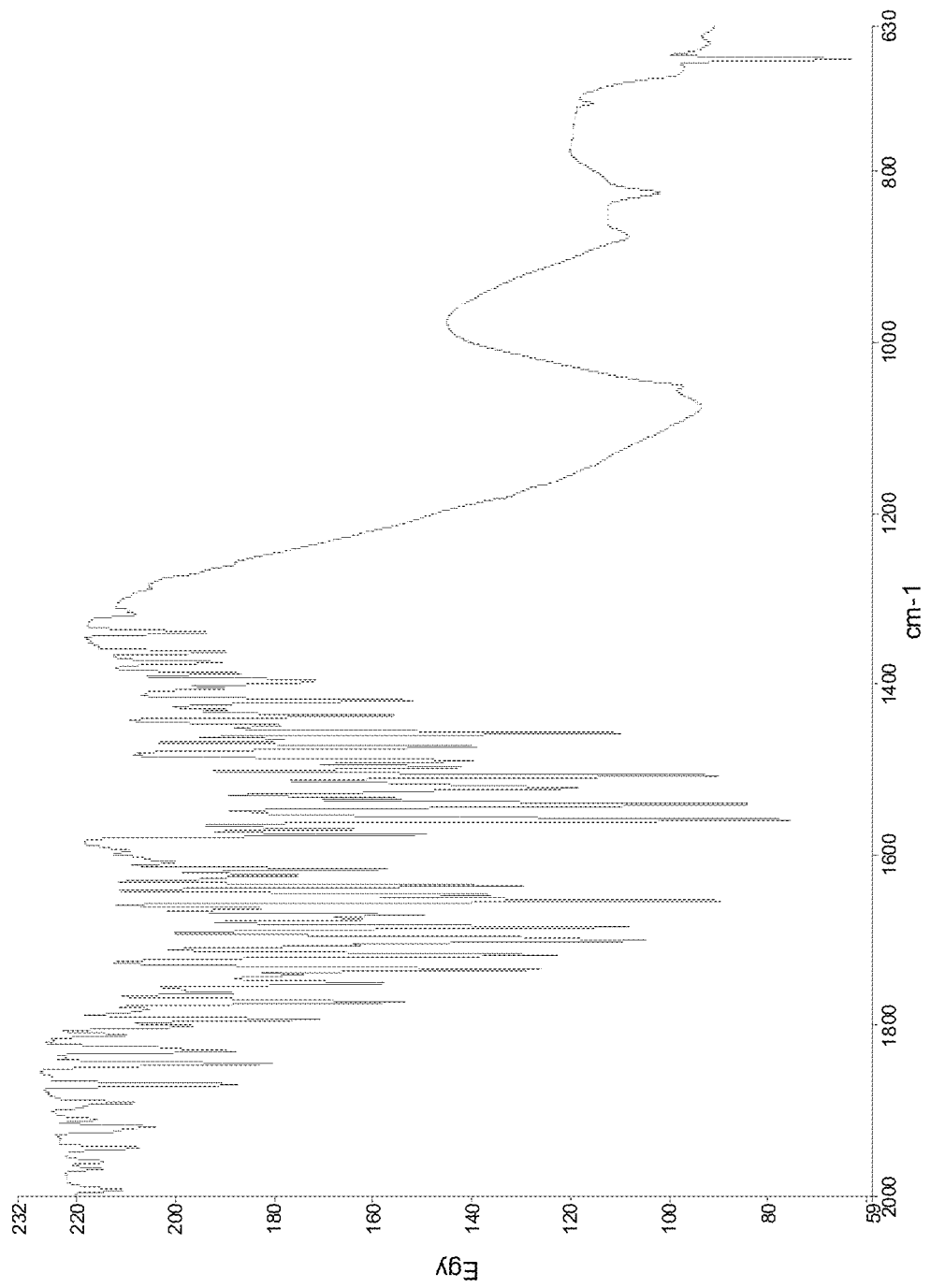
FIGS. 10A, 10B, and 10C show detector curves over a range of interest of wavenumbers for a typical FTIR spectrometer (FIG. 10A), for an ATR crystal 702 such as described with respect to and shown in FIG. 7 (FIG. 10B), and for a Fiber Loop Probe 6 such as described with respect to and shown in FIG. 1 (FIG. 10C).
Figure 10B:
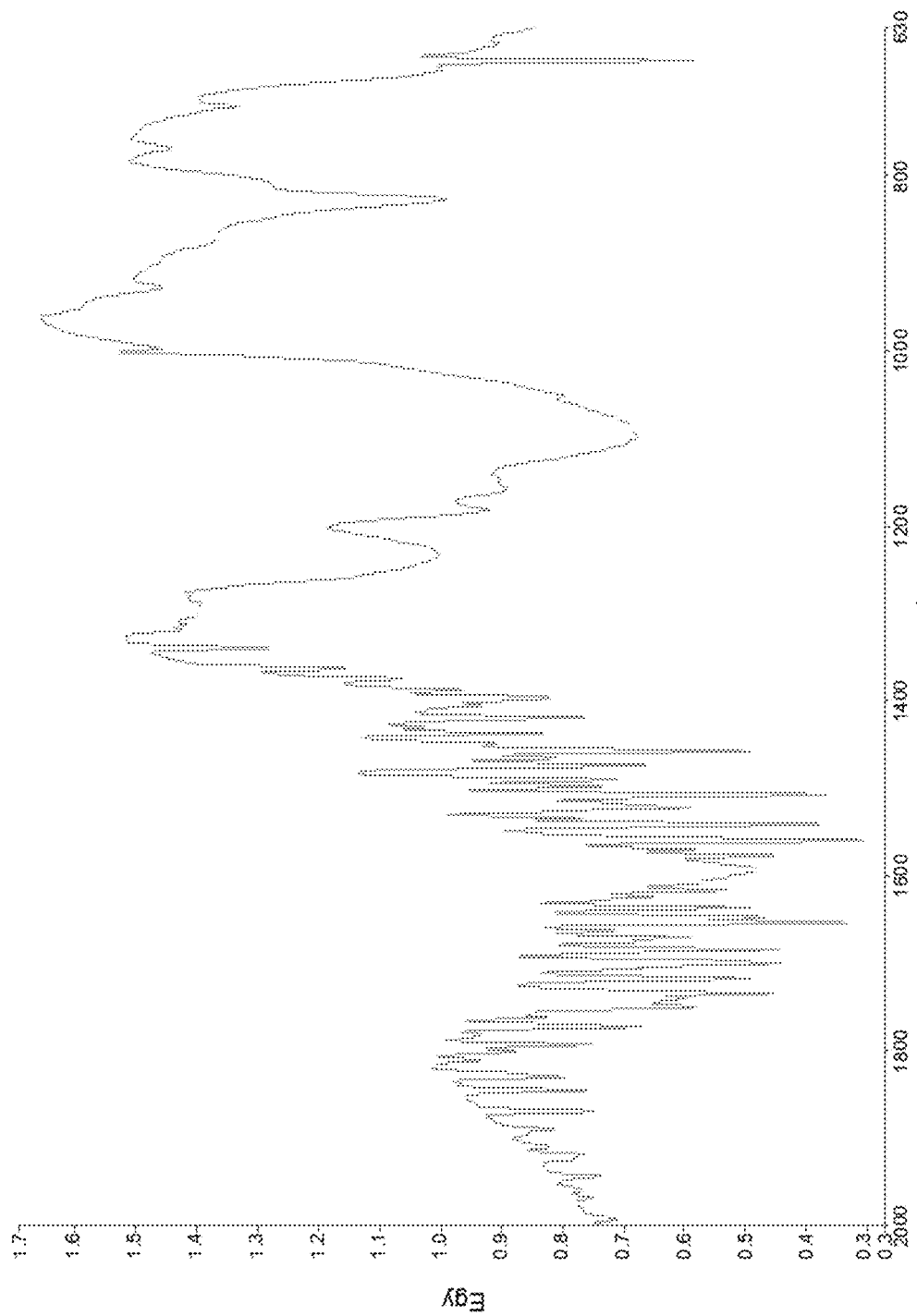
Figure 10C:
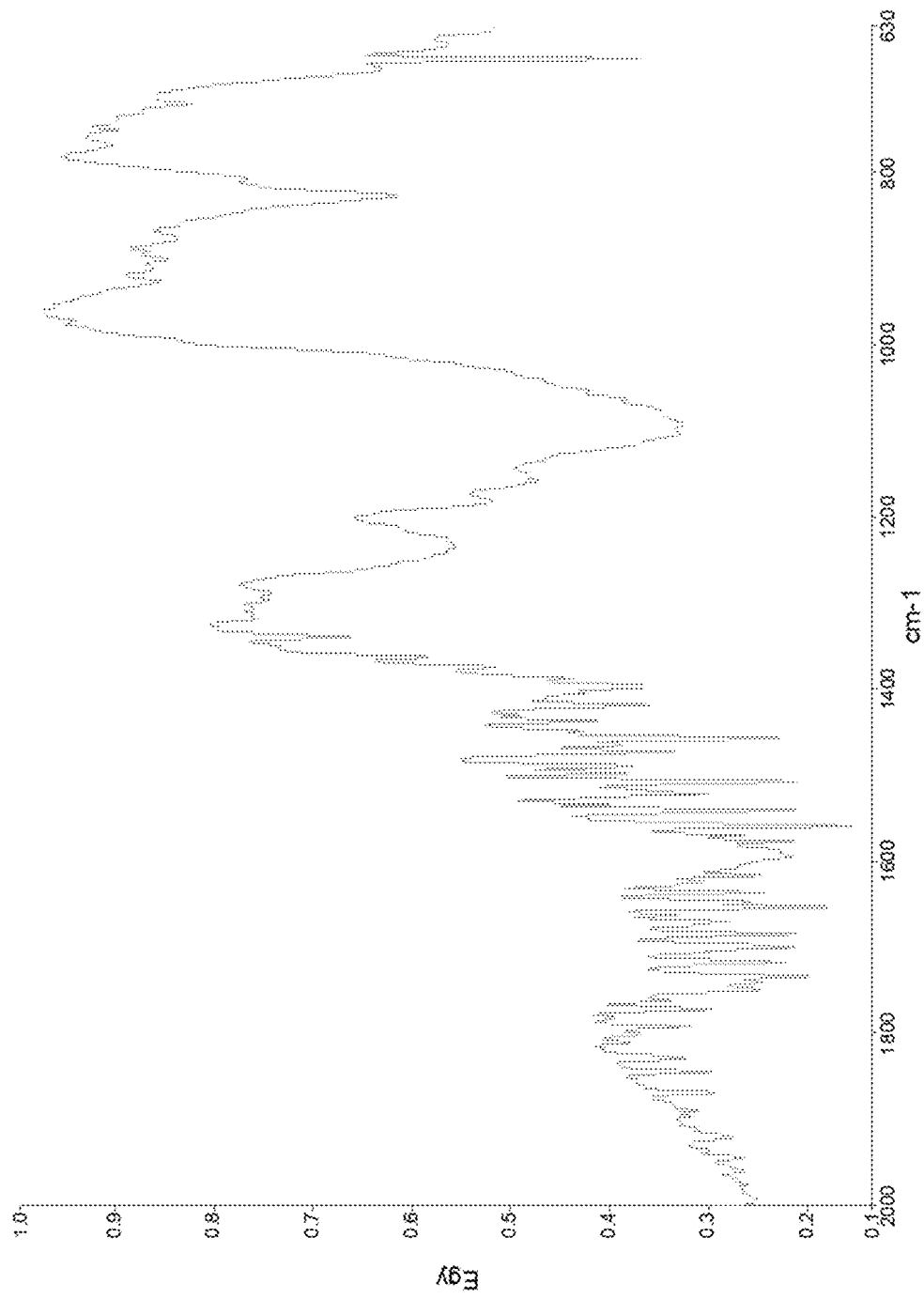

FIGS. 10A, 10B, and 10C show detector curves over a range of interest of wavenumbers for a typical FTIR spectrometer (FIG. 10A), for an ATR crystal 702 such as described with respect to and shown in FIG. 7 (FIG. 10B), and for a Fiber Loop Probe 6 such as described with respect to and shown in FIG. 1 (FIG. 10C). As shown in the data of FIGS. 10A-10C, with respect to the FTIR spectrometer, the ATR response is attenuated by a factor of 139 at a wavenumber of 1400 $cm^{-1}$ and is attenuated by a factor of 88 at a wavenumber of 1000 $cm^{-1}$, and the Fiber Loop Probe is attenuated by a factor of 269 at a wavenumber of 1400 $cm^{-1}$ and is attenuated by a factor of 165 at a wavenumber of 1000 $cm^{-1}$. In sum, etalon fringes can still be detected using the ATR response arrangement shown in FIG. 7, but more sensitive detector components or more intense etalon illumination may be helpful to permit detection using the Fiber Loop Probe arrangement shown in FIG. 1.

Examples of Some Variations

A variety of variations can be made to the subject matter as disclosed herein. For example, the light source 1 can be any broadband light source—no laser light source is required. Examples of light source 1 can include another light source that can emit white light such as, for example, a light bulb that is purged by argon. The broadband light source can include enough wavelengths for covering the wavelengths of interest for tissue illumination, response detection, and spectroscopic analysis. The etalon 3 can be used to vary the emitted fringe wavelengths. For example, the etalon 3 can change fringe wavelengths by angle tuning the etalon 3, by change of spacing d of the etalon, and the like. The optical coupler 4 need not use a lens coupling. For example, various IR transmissive materials with various optical properties can be used, or free space (direct transmission into an assembly) optical coupling can be used. The fiber optic 5 connection need not feed light directly into the probe 6. For example, as an alternative to refractive lens coupling by the optical coupler 4, reflective coupling can be used, such as using a set of concave reflective mirrors (e.g., gold or silver or aluminum) or the like.

The connection to the probe 6 can be altered to, for example, a solid material, an IR transmissive material connected to the optical coupler 4, or nothing—in which case the beam emerging from the etalon 3 will diverge but is configured such that enough electromagnetic energy of the emerging fringes will get to the probe 6. The IR Fiber Loop Probe 6 can be different than a single loop. For example, the probe can have more than 1 loop, or can have loops in different locations, such as an array of loops or other configuration that can allow parallel illumination and acquisition of tissue response data, such as for performing imaging or similar spatial analysis of the different locations. The probe tip shape and composition can be different than shown. The probe tip can include an optical diffuser, such as to promote diffuse scattering of photons within the tissue sample or specimen 102, or can use a variety of ATR crystals. The probe tip can include different shapes, for example, such as hemispherical or angled on edge. Also, the composition of the probe tip can vary, such as diamond, KBr, ZnSe, Ge, Si, or the like.

The diffraction grating 9 and the parallel array detector 10 can employ other spectral dispersion techniques, such as can include using a prism, a series of wavelength-selective optical filters, or an angle tuned grating or prism, and can then use a single mid-infrared light detector (e.g., need not use an array of pixels). A FT interferometer could be used instead of the foregoing dispersive designs. In such an example case, an interferometer with moving mirrors would change the pathlength of the IR light and be detected in time, and then back correlated to the frequency/wavelength through Fourier Transform.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A computer-assisted method of discriminating tissue of a tissue specimen, the computer-assisted method comprising:
    illuminating a location of the specimen using an etalon with a specified spacing between plates to selectively generate a set of multiple specified illumination fringe wavelengths from a broadband source for concurrent delivery to the location of the specimen;
    in response to the illuminating, receiving an electromagnetic energy response signal, the response signal including respective specified response signal wavelengths corresponding to the specified illumination fringe wavelengths;
    spectrally dispersing the received electromagnetic energy response signal over individual detector pixels in a parallel detector array of individual detector pixels respectively corresponding to individual ones of the specified response signal wavelengths for concurrent detection by the parallel detector array;
    concurrently detecting the spectrally dispersed received electromagnetic energy response signal using the individual detector pixels in the parallel detector array and storing corresponding resulting electromagnetic energy response signal data; and
    using a computing device, the stored electromagnetic energy response signal data, and a trained model to process electromagnetic energy response wavelengths to be analyzed, discriminating between at least two tissue classification categories of the location of the specimen.

2. The computer-assisted method of claim 1, wherein at least one of the illuminating or the receiving the electromagnetic energy response signal includes using at least one of a Fiber Loop probe or an Attenuated Total Reflection (ATR) crystal to interface with the specimen.

3. The computer-assisted method of claim 1, wherein the spectrally dispersing includes diffracting.

4. The computer-assisted method of claim 3, wherein the spectrally dispersing includes diffracting using more than one diffraction grating.

5. The computer-assisted method of claim 1, comprising reflecting the received electromagnetic energy response signal in an electromagnetic energy signal pathway between the specimen and the parallel detector array.

6. The computer-assisted method of claim 5, wherein the reflecting is toward a respective one of one or more diffraction gratings.

7. The computer-assisted method of claim 1, wherein using the trained model includes using a model trained using a computing device and spectral data over a fuller wavenumber set to develop a Support Vector Machines (SVM) beta spectrum used for selecting a reduced set of equally-spaced wavenumbers output from a particular etalon.

8. The computer-assisted method of claim 1, comprising using at least one of multiple mirrors, multiple diffraction gratings, or multiple parallel array detectors in an electromagnetic energy pathway from the specimen.

9. The computer-assisted method of claim 1, comprising establishing the specified spacing using a user-adjustably variable spacer to obtain a user-adjustable variable distance between plates of the etalon.

10. A system for discriminating tissue of a tissue specimen, the system comprising:
an electromagnetic energy illuminator, arranged for illuminating a location of the specimen, the illuminator including an etalon with a specified spacing between plates to selectively generate a set of multiple specified illumination fringe wavelengths from a broadband source for concurrent delivery to the location of the specimen;
an electromagnetic energy response detector, configured for, in response to the illuminating, receiving an electromagnetic energy response signal, the response signal including respective specified response signal wavelengths corresponding to the specified illumination fringe wavelengths, wherein the electromagnetic energy response detector includes:
a spectral dispersion component, configured for spectrally dispersing the received electromagnetic energy response signal; and
individual detector pixels in a parallel detector array of individual detector pixels respectively corresponding to individual ones of the specified response signal wavelengths for concurrent detection by the parallel detector array, the individual detector pixels arranged for concurrently detecting and transducing the spectrally dispersed received electromagnetic energy response signal using the individual detector pixels in the parallel detector array; and
a computing device, including a signal processor configured for, using a trained model to process electromagnetic energy response wavelengths transduced by the individual detector pixels to be analyzed and used for discriminating between at least two tissue classification categories of the location of the specimen, and for providing an output indication of the discrimination.

11. The system of claim 10, wherein at least one of the electromagnetic energy illuminator or the electromagnetic energy response detector includes at least one of a Fiber Loop probe or an Attenuated Total Reflection (ATR) crystal arranged to interface with the specimen.

12. The system of claim 11, wherein the spectral dispersion component includes a diffraction grating.

13. The system of claim 12, wherein the spectral dispersion component includes more than one diffraction grating arranged to disperse, toward respective individual detector pixels of a parallel detector array, respective electromagnetic energy response detector wavenumbers of the electromagnetic energy response signal corresponding to respective electromagnetic energy illumination wavenumbers of fringes output by the etalon.

14. The system of claim 10, comprising at least one reflector arranged for reflecting the received electromagnetic energy response signal in an electromagnetic energy signal pathway between the specimen and the parallel detector array.

15. The system of claim 14, wherein the at least one reflector is arranged for reflecting toward a respective one of one or more diffraction gratings.

16. The system of claim 10, wherein trained model includes a model trained using a computing device and spectral data over a fuller wavenumber set to develop a Support Vector Machines (SVM) beta spectrum used for selecting and providing a reduced set of equally-spaced wavenumbers output from the etalon for use during run-time testing of the specimen.

17. The system of claim 10, comprising least one of multiple mirrors, multiple diffraction gratings, or multiple parallel array detectors in an electromagnetic energy pathway of the electromagnetic energy response signal from the specimen.

18. The system of claim 10, comprising a user-adjustable variable spacer to establish a specified spacing between components of the etalon.

19. The system of claim 10, wherein the spectral dispersion component includes a reflective diffraction granting.

20. A system for discriminating tissue of a specimen, the system comprising:
means for illuminating a location of the specimen using an etalon with a specified spacing between plates to selectively generate a set of multiple specified illumination fringe wavelengths for concurrent delivery to the location of the specimen;
an electromagnetic energy response detector configured for, in response to the illuminating, receiving an electromagnetic energy response signal, the response signal including respective specified response signal wavelengths corresponding to the specified illumination fringe wavelengths;
means for spectrally dispersing the received electromagnetic energy response signal over individual detector pixels in a parallel detector array of individual detector pixels respectively corresponding to individual ones of the specified response signal wavelengths for concurrent detection by the parallel detector array;
means for concurrently detecting and transducing the spectrally dispersed received electromagnetic energy response signal using the individual detector pixels in the parallel detector array; and
a computing device including or using a trained model to process electromagnetic energy response wavelengths to be analyzed for discriminating between at least two tissue classification categories of the location of the specimen.

* * * * *